United States Patent
Mohan et al.

(10) Patent No.: US 8,283,323 B2
(45) Date of Patent: Oct. 9, 2012

(54) WITHANOLIDE COMPOUNDS AS INHIBITORS OF FIBROSIS AND IDENTIFICATION OF MOLECULAR TARGETS FOR ANTI-FIBROTIC DRUG DEVELOPMENT

(75) Inventors: Royce Mohan, Lexington, KY (US); Paola Bargagna-Mohan, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 162 days.

(21) Appl. No.: 11/724,053

(22) Filed: Mar. 13, 2007

(65) Prior Publication Data

US 2008/0032958 A1 Feb. 7, 2008

Related U.S. Application Data

(60) Provisional application No. 60/781,973, filed on Mar. 13, 2006.

(51) Int. Cl.
*A61P 27/02* (2006.01)
*A61K 36/185* (2006.01)

(52) U.S. Cl. ........... 514/20.8; 514/169; 435/15; 435/29; 424/725; 548/454

(58) Field of Classification Search .................. 514/169, 514/20.8; 435/15, 29; 424/725; 548/454
See application file for complete search history.

(56) References Cited

U.S. PATENT DOCUMENTS

2004/0033273 A1  2/2004  Patwardhan et al.
2004/0096524 A1*  5/2004  Nair et al. ..................... 424/725

OTHER PUBLICATIONS

Frungieri et al, Proliferative action of mast-cell tryptase is mediated by PAR2, COX2, prostaglandins, and PPAR gamma, possible relevene to human fibrotic disorders., PNAS, vol. 99(23), 2002.*
Comer et al. Current and Future pharmacological intervention of diabetic retinopathy, Expert opinion Emerging drug (2005), 10(2), 441-455.*
Choi et al. Ixocarpalactone A isolated form the mexican tomatillo shows potent antiproliferative adn apoptotic activity in colon cancer cells, FEBS Journal, 273, 2006, pp. 5714-5723.*
Radisky et al, Fibrosis and Cancer: Do myofibroblasts come also from Epitheilal cells viw EMT, Journal of cellular biochemistry 101, 830-839 (2007).*
Chatterjee S. et al. Antonie Van Leeuwenhoek 46, 1980, 59-63.*

* cited by examiner

*Primary Examiner* — Savitha Rao
(74) *Attorney, Agent, or Firm* — Crowell & Moring LLP

(57) ABSTRACT

Provided are methods for screening for drugs effective for treating fibrotic conditions. One screening method comprises exposing a cell to a test compound, monitoring the effect of the test compound on the amount or form of a cell molecule, comparing the amount or form of the cell molecule with the result obtained by treatment of the cell with an anti-fibrotic - effective amount of a withanolide compound, and selecting a drug effective for treating a fibrotic disease based on the ability of the test compound to provide the effect obtained by the withanolide compound on the cell molecule. Also provided is a method of treating a fibrotic disease comprising administering an anti-fibrotic effective amount of a withanolide compound to a mammal in need of treatment for fibrosis.

7 Claims, No Drawings

WITHANOLIDE COMPOUNDS AS INHIBITORS OF FIBROSIS AND IDENTIFICATION OF MOLECULAR TARGETS FOR ANTI-FIBROTIC DRUG DEVELOPMENT

CROSS-REFERENCE TO RELATED APPLICATIONS

This application claims priority to U.S. Provisional Application No. 60/781,973, filed Mar. 13, 2006, which is incorporated herein in its entirety.

FIELD OF THE INVENTION

The present invention relates to methods of screening compounds for treating fibrosis and to methods for treating fibrosis.

DESCRIPTION OF THE RELATED ART

Fibrosis is a deviant process of tissue repair. It is a serious complication after major surgical procedures and organ transplants, and can also occur during cancerous growth, endometriosis, alcohol-related liver damage, cardiovascular disease, retinal detachment, and other disorders. Thus, fibrogenic complications contribute to the pathogenesis of many common and devastating diseases and yet there is no effective treatment for this chronic problem. Hence, an unaddressed need exists in the industry to address the aforementioned deficiencies and inadequacies.

SUMMARY OF THE INVENTION

In one embodiment, the invention provides a method of screening for a drug effective for treating a fibrotic disease. The method comprises exposing a cell to a test compound, monitoring the effect of the test compound on the amount or form of a cell molecule, comparing the amount or form of the cell molecule with the result obtained by treatment of the cell with an anti-fibrotic-effective amount of a withanolide compound, and selecting a drug effective for treating a fibrotic disease based on the ability of the test compound to provide the effect obtained by the withanolide compound on the cell molecule.

In another embodiment, the invention provides a method of screening for a drug effective for treating a fibrotic disease. The method comprising exposing a cell to a test compound, monitoring the effect of the test compound on the intracellular activity of the ubiquitin proteasome pathway (UPP), comparing the intracellular activity of the UPP with the result obtained by treatment of the cell with an anti-fibrotic-effective amount of a withanolide compound, and selecting a drug effective for treating a fibrotic disease based on the ability of the test compound to provide the effect obtained by the withanolide compound on the UPP.

In yet another embodiment, the invention provides a method of treating a fibrotic disease comprising administering an anti-fibrotic effective amount of a withanolide compound to a mammal in need of treatment for fibrosis. Also provided is a composition for the treatment of fibrosis comprising a withanolide compound which inhibits intracellular ubiquitination of transketolase.

DESCRIPTION OF PREFERRED EMBODIMENTS

The invention relates generally to methods for treating fibrotic conditions and to procedures for identifying drugs for the treatment of fibrotic conditions.

Any fibrotic condition can be the subject of the invention, such as the fibrosis that is associated with organ failure in a variety of chronic diseases affecting the lungs, kidney, eyes, heart, liver and skin. Such fibrotic conditions include diabetic nephropathy, glomerulosclerosis, IgA nephropathy, diabetic retinopathy, advanced macular degeneration, liver cirrhosis and biliary atresia, congestive heart failure, endomyocardial fibrosis, idiopathic myocardiopathy, lung fibrosis, diffuse parenchymal lung disease, mediastinal fibrosis, progressive massive fibrosis, fibrosis of the lungs associated with tuberculosis, scleroderma, fibrosis associated with cancerous growth, endometriosis, fibrosis associated with surgery, alcohol-related liver damage, cardiovascular disease, and retinal detachment.

The present inventors have discovered that inflammation and fibrosis are associated with activation of the inflammatory transcription factor NF-kappa-B, a key mediator of cytokine gene activation and immune regulation. Activation of NF-kappa-B occurs in coordination with increases in the biochemical activities of the ubiquitin proteasome pathway (UPP), the principal machinery for intracellular protein degradation. Inhibiting the UPP via an appropriate inhibitor is used according to the present invention to identify compounds which are effective for treating fibrosis. Inhibition of the UPP is also associated with a reduction in the level of ubiquitinated transketolase in the cell. In another embodiment, the effect of a test compound on a cell molecule is compared with the effect of a withanolide compound to determine whether the test compound is effective for treating a fibrotic disease. Also described is a method of treating fibrosis via administration of a UPP-inhibitory compound. In one embodiment, a fibrotic condition is treated by administration of a withanolide compound.

The methods of the present invention can be used with any mammalian species, including human, monkey, cow, sheep, pig, goat, horse, mouse, rat, dog, cat, rabbit, guinea pig, hamster and horse. Humans are preferred.

In performing screening procedures for identifying UPP-inhibitory compounds, any mammalian cell, tissue or organ can be used according to the present invention. Such screening procedures can be performed in vitro or in vivo. For example, cells in culture can be exposed to a test compound for evaluation as to whether the test compound possesses UPP-inhibitor activity. In another embodiment, test compound can be administered to a subject, and then cells, a tissue or an organ can be removed from the subject and then be evaluated as to whether the test compound possesses UPP-inhibitory activity.

Appropriate mammalian cells for use in the screening procedures of the invention include, by way of example, neural cells, epithelial cells, epidermal cells, keratinocytes, hematopoietic cells, melanocytes, chondrocytes, lymphocytes (B and T lymphocytes), erythrocytes, macrophages, monocytes, mononuclear cells, fibroblasts, hepatocytes, cardiac muscle cells or other muscle cells, or a corneal cell, choroidal cell or any other cell of the eye, etc. Cells which can be used include all somatic or germ cells. Moreover, any mammalian organ or cells from any organ may be used, e.g., eye, brain, skin, lung, pancreas, liver, stomach, intestine, esophagus, spleen, thymus, thyroid gland, salivary gland, bone, heart, skeletal muscle, reproductive organs, bladder, kidney, urethra and other urinary organs, etc.

Withanolide compounds are inhibitors of the UPP. Thus, in evaluating whether a test compound possesses anti-fibrotic activity, the effect of a test compound can be compared with the effect of a withanolide compound.

Withanolides were first characterized as bioactive substances present in the plant *Withania somnifera*. Chemically, withanolides are steroidal lactones. Exemplary withanolides which possess UPP-inhibitory activity include withaferin A, withanolide D and ixocarpalactone A. In general, withanolides which possess UPP-inhibitory activity have a steroid structure with an alpha, beta-unsaturated ketone in the A ring, a 4-beta-hydroxy substituent, a 5,6 beta-epoxide, and a 5- or 6-member lactone substituent attached to the D ring.

The present invention also provides a method of treating a fibrotic disease, comprising administering an anti-fibrotic effective amount of a withanolide compound to a mammal in need of treatment for fibrosis. Such fibrotic diseases include any of the conditions enumerated above.

According to the method of the invention, one or more withanolide compounds can be administered to the host by an appropriate route, either alone or in combination with another drug. An effective amount of a withanolide compound is administered. An effective amount is an amount sufficient to achieve the desired therapeutic effect, under the conditions of administration, such as an amount sufficient for inhibition of the UPP, and thereby effectively treat fibrosis.

A variety of routes of administration are possible including, but not necessarily limited to oral, dietary, topical, parenteral (e.g., intravenous, intraarterial, intramuscular, subcutaneous injection), inhalation (e.g., intrabronchial, intranasal or oral inhalation, intranasal drops), and intraocular injection routes of administration, depending on the disease or condition to be treated. Intraocular injection routes include periocular (subconjunctival/transscleral), intravitreous, subretinal and intracameral modes of injection.

Formulation of a withanolide compound to be administered will vary according to the route of administration selected (e.g., solution, emulsion, capsule). An appropriate composition comprising the withanolide compound to be administered can be prepared in a physiologically acceptable vehicle or carrier. The withanolide compound compositions of the invention include sustained release formulations. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, Remington's Pharmaceutical Science, 16th Edition, Mack, Ed. 1980). For inhalation, the withanolide compound is solubilized and loaded into a suitable dispenser for administration (e.g., an atomizer, nebulizer or pressurized aerosol dispenser).

Studies of Fibrosis in the Eye

The eye is among the organs in which fibrosis can occur. Tissue repair in the cornea usually occurs through a regenerative mechanism which helps the cornea regain its optical function. This property has made corneal transplant surgery and vision corrective surgical procedures a great success. However, alkali burn injuries, severe mechanical trauma and infectious agents can cause corneal fibrosis, and it is this impaired form of tissue repair that results in blindness. Since the cornea can feature a regenerative or fibrotic phenotype based on the type of injury, this tissue serves as an excellent model to study the molecular mechanisms of fibrosis.

Corneal wound healing is a tightly coordinated process that must regenerate the biological and optical functions of this refractive tissue. This process is coordinated through autocrine and paracrine interactions of growth factors, cytokines and proteases produced by the stromal keratocytes, epithelial cells and lacrimal gland cells. It has been suggested that the inflammation transcription factor NF-kappaB plays a role in tissue repair by controlling cytokine autocrine loops, i.e., IL-1-alpha expression. IL-1-alpha is a potent stimulator of collagenase gene expression, and its overproduction is observed in trauma situations such as alkali and thermal burn, which can cause severe tissue maceration due to uncontrolled production of stromal collagenase. Thus silencing of NF-kappaB may be a requirement for maintenance of corneal clarity, immune deviation and avascularity during tissue repair. However, what signals overcome the competence to activate NF-kappaB when corneal tissue is injured has remained elusive.

Recently, using the keratocyte and fibroblast culture model as representative of regenerative and fibrogenic repair mechanisms, respectively, Stramer et at (*Invest. Ophthalmol. Vis. Sci.*, 42(8):1698-1706, 2001) showed that transition to the repair fibroblast phenotype during the 3 days after initial plating is coincident with progressive induction of the ubiquitin proteasome pathway (UPP). Levels of free ubiquitin (Ub), Ub-conjugated proteins, ubiquinylating enzymes E1 and E2-25K, and 26S proteasome were increased 2-5-fold in stromal cells as they transitioned from the keratocyte phenotype into repair fibroblast phenotype. These increases were associated with enhanced (>10-fold) capacity for Ub-dependent proteolysis. The levels of native I-kappa-B-alpha, but not that of its phosphorylated form, was elevated in activated fibroblasts compared to keratocytes, suggesting that the constitutive activation of NF-kappaB promotes native I-kappa-B-alpha synthesis but, due to increased proteasome activity, the inhibitory form (phosphorylated I-kappa-B-alpha) is rapidly degraded. Both freshly isolated and activated fibroblasts degraded I-kappa-B-alpha in response to IL-1-alpha; yet, only activated fibroblasts maintained autocrine IL-1-alpha expression after 24 hours. These authors conclude that coordinate induction of the UPP during fibroblast activation that causes activated I-kappa-B-alpha to be rapidly degraded may drive the autocrine IL-1-alpha loop, perpetuating a chronic state of inflammation. Since the UPP regulates NF-kappaB activation through its orchestrated degradation of I-kappa-B-alpha, the cytoplasmic inhibitor of NF-kappaB, targeting the UPP may be a novel means of downregulating corneal fibrosis. The UPP has become the center of great attention because of its critical role in inflammation and fibrovascular growth, and as an important source of multiple sites for pharmacological targeting.

The abundant corneal protein tissue transketolase (TKT) is believed to play an important role in corneal homeostasis. TKT is also a target of the UPP and its reduced expression is believed to contribute to corneal fibrosis. In the present invention, targeting the UPP in injured tissue can redirect the fibrotic repair process to acquire regenerative healing. Withanolides and related compounds, such as withaferin A, withanolide D and ixocarpalactone, are small molecule inhibitors that have potent UPP-targeting activity. Exposure to withaferin A causes potent downregulation of UPP functions in the alkali burn injury model of corneal angiofibrotic disease. There is also a reduction in the levels of ubiquitinated transketolase (TKT), an abundant corneal protein implicated in fibrogenesis.

EXAMPLE 1

The corneas of C57BL6 mice under anesthesia were injured by application of 0.1 N sodium hydroxide and subsequently the epithelial cell layer from the cornea and limbus was removed by scraping. Withaferin A (WA) (2.5 mg/kg/d; 4 mice) or vehicle (DMSO; 4 mice) was provided daily thereafter by i.p. injection for 6 d. Digital images of the corneas were obtained to assess the extent of tissue pathology. Vehicle-treated mice display profound corneal opacity and abundant growth of new blood vessels, whereas in WA-treated mice both the corneal opacity and neovascularization are dramatically reduced. These compelling results invoke the query whether WA targets the UPP in vivo. Mice (4 per group) were injured and treated for the first 4 days with a different dose of WA or vehicle daily by i.p. injection. On day 7, mice were sacrificed and corneal buttons were isolated from injured healing corneas; equal amounts of protein from each group were analyzed by western blotting. Uninjured fellow eyes from vehicle-treated mice served as controls.

We discovered that WA dose-dependently inhibits corneal expression of native I-kappa-B-alpha, whereas expression of native I-kappa-B-alpha in vehicle-treated mice was highly elevated compared to uninjured corneas. We also assessed the expression levels of HO-1, since its expression is upregulated by angiogenic inducers during response to inflammation. WA potently downregulated HO-1 expression to almost undetectable levels as found in uninjured corneas. These findings that inhibition of I-kappa-B-alpha and HO-1 expression by WA hence corroborate the potent pharmacological activity of WA an inhibitor of angiofibrosis.

EXAMPLE 2

WA Reduces Injury-Induced Expression of Ubiguitinated Transketolase in the Cornea During tissue injury, TKT expression is downregulated in a UPP-dependent manner as the tissue progresses into fibrosis. To investigate the levels and timing of expression of TKT we performed time-course experiments using the angioinflammation corneal model of tissue repair. Groups of mice (n=0.3/group) were injured and treated every day with vehicle (Veh), 2.5 mg/kg/d WA or 2.0 mg/kg/d epoxomicin (20S proteasome inhibitor) and sacrificed on day 4 and 6 post-inflammation. In a similar experiment, mice were treated every day with vehicle or 2.5 mg/kg/d WA and sacrificed on days 3 and 5 post-injury. Equal amounts of protein from pooled samples of each group were subjected to immunoblotting or Coomassie blue staining after fractionation on 4-20% gradient polyacrylamide gels (BioRad).

We observed that a 70 kDa ubiquitinated protein was abundantly expressed in vehicle-treated mouse corneas compared to corneas from WA-treated mice. Coomassie blue staining, however, revealed that the levels of this protein were not significantly altered between uninjured, vehicle and WA-treated samples at the 3- and 5-day time-points, or at the 4- and 6-day time-points examined (data not shown). The western blots of the corneal samples were re-probed with an anti-mouse TKT antibody. We discovered that the uninjured corneas expressed high levels of TKT as anticipated, but surprisingly TKT from injured corneas did not bind this antibody. Because of the strong Ub-immunoreactivity of TKT in injured corneas, we speculate that this protein's N-terminal antigenic site is being masked by ubiquitination in the injury-related samples (the TKT antibody reacts with the N-terminal 20-amino acid portion of native TKT). Our findings are consistent with an earlier study that also failed to detect UbTKT in fibrotic cells. We believe that TKT is conjugated with mono-ubiquitin species, rather than polyubiquitin species, because the ubiquitin immunoreactivity of the 70 kDa protein does not smear all the way up to the top of the gel.

Exposure of blots to X-ray film for slightly longer periods of time (30-40 seconds instead of 5 minutes) revealed the presence of the TKT in WA- and epoxomicin-treated corneas, but not in vehicle-treated mouse corneas. To investigate the localization of TKT, immunohistochemical analysis of mouse eyes was conducted. TKT expression is localized to the epithelium of uninjured mouse eyes, whereas TKT expression in corneas of 4 d vehicle-treated mice is almost undetectable. Staining in corneas of WA-treated mice was present, although at levels lower than that of uninjured cornea, with staining being predominantly in the epithelium, and very little in the stroma.

This data is consistent with the general idea that ubiquitinated proteins are generated in the corneal epithelium upon alkali burn injury as a result of oxidative damage, and removal of these damaged proteins is enabled by upregulation of the UPP. The persistent high amount of UbTKT in injured corneas suggests that this protein is being retained in a posttranslationally-modified state.

The prevailing hypothesis is that TKT plays a role in supporting regenerative healing and response to environment stress. Our finding that uninjured mouse corneas also express UbTKT, although at low levels, indicates that this variant is physiologically removed by the UPP, and that overexpression during severe tissue inflammation promotes fibrosis. Hence, TKT is a new molecular target for anti-fibrosis drug development. Moreover, withaferin A and related withanolides can be used to treat fibrotic conditions

EXAMPLE 3

Anti-Fibrogenic in vivo Activity of Withaferin A

Under full anesthesia and application of topical ocular anesthetic solution, a 1-mm full-thickness button of central corneal tissue, including all three layers—epithelium, stroma and endothelium—is ablated and the area is carefully scored by insertion and removal of a 26-gauge needle into the central cornea employing the use of a dissecting microscope. The full-thickness tissue button that is demarcated by the needle insertion is removed with microdissecting scissors. After approximately 15 minutes, a fibrin clot forms in this space, enabling the anterior chamber to reform. The cornea is coveted with erythromycin and tobramycin ophthalmic ointment to prevent infections. Atropine is administered once daily for two days. The corneal tissue is harvested after 2, 5 and 8 days.

In the first experiment, the dose-response of corneal fibrogenesis to the inhibitory activity of WA in C57 BL/6J mice is determined. The drug is freshly diluted in 1:1 saline:DMSO and delivered by i.p. injection. Vehicle and WA at doses of 0.5, 2.0, 5.0 and 12.0 mg/kg/d are administered for 7 or 14 days (4 mice/group/time point). A second experiment is terminated on days 3, 7, 10 and 14 (6 mice/group/time point) and employs an effective WA dose determined from experiment 1, as well as vehicle controls.

Mice are visually scored for corneal opacity on days 7 and 14 by employing an investigator masked to the identity of the treatment groups. Digital photographic images of corneas are also collected. These visual scores are corroborated by immunohistological and western blot analyses of mouse corneas after 7 days (for 3- and 7-day treatment) and 14 days (for 10- and 14-day treatment). Three mouse corneas are employed for western blots and three for sectioning. The immunohistological analysis includes hematoxylin-eosin staining, alpha-smooth muscle actin (marker of repair fibroblast-myofibroblasts), phalloidin (filamentous actin stress fibers), TGF-beta2 (myofibroblast-differentiation inducer), Mac-1 staining (marker of monocytes and PMNs), HO-1, I-kappa-B-alpha and ubiquitin using frozen sections. For western blotting, HO-1, I-kappa-B-alpha, ubiquitin, TKT, alpha-smooth muscle (sm) actin and TGF-beta2 expression are analyzed.

All references cited in this disclosure are incorporated by reference to the same extent as if each reference had been incorporated by reference in its entirety individually.

While the invention has been described in detail and with reference to specific embodiments thereof, it will be apparent to one skilled in the art that various variations and modifications can be made therein without departing from the sprit and scope thereof. All such variations and modifications are intended to be included within the scope of this disclosure and the present invention and protected by the following claims.

We claim:

1. A method of treating a fibrotic disease in a mammal comprising administering an anti-fibrotic effective amount of a withanolide compound to a mammal in need of treatment for fibrosis of the eye wherein the anti-fibrotic effective amount is 0.5 to 12 mg/kg/day.

2. The method of claim 1 wherein the withanolide compound is withthaferin A.

3. The method of claim 1 wherein the withanolide compound is withthanolide D.

4. The method of claim 1 wherein the withanolide compound is ixocarpalactone A.

5. The method of claim 1 wherein the withanolide compound is orally administered to the mammal.

6. The method of claim 1 wherein the withanolide compound is intravenously administered to the mammal.

7. The method of claim 1 wherein the withanolide compound is intraocularly injected into the mammal.

* * * * *